(12) United States Patent
Pankalla et al.

(10) Patent No.: US 11,774,394 B2
(45) Date of Patent: Oct. 3, 2023

(54) ELECTROCHEMICAL SENSOR AND SENSOR SYSTEM FOR DETECTING AT LEAST ONE ANALYTE

(71) Applicant: Roche Diabetes Care, Inc., Indianapolis, IN (US)

(72) Inventors: Sebastian Pankalla, Mannheim (DE); Jonathan Seidel, Mannheim (DE); Tommi Kaehkoenen, Mannheim (DE)

(*) Notice: Subject to any disclaimer, the term of this patent is extended or adjusted under 35 U.S.C. 154(b) by 55 days.

(21) Appl. No.: 16/820,416

(22) Filed: Mar. 16, 2020

(65) Prior Publication Data
US 2020/0217814 A1 Jul. 9, 2020

Related U.S. Application Data

(63) Continuation of application No. PCT/EP2018/075031, filed on Sep. 17, 2018.

(30) Foreign Application Priority Data

Sep. 18, 2017 (EP) .................... 17191602

(51) Int. Cl.
| G01N 27/327 | (2006.01) |
| C12Q 1/00 | (2006.01) |
| C12Q 1/32 | (2006.01) |

(52) U.S. Cl.
CPC ......... *G01N 27/3272* (2013.01); *C12Q 1/006* (2013.01); *C12Q 1/32* (2013.01); *G01N 27/3273* (2013.01)

(58) Field of Classification Search
None
See application file for complete search history.

(56) References Cited

U.S. PATENT DOCUMENTS

| 4,655,880 A | 4/1987 | Liu |
| 5,413,690 A | 5/1995 | Kost et al. |
(Continued)

FOREIGN PATENT DOCUMENTS

| CN | 102149315 A | 8/2011 |
| CN | 102507695 A | 6/2012 |
(Continued)

OTHER PUBLICATIONS

International Preliminary Report on Patentability, PCT/EP2018/075031, dated Dec. 17, 2019, 8 pages.
(Continued)

*Primary Examiner* — J. Christopher Ball
(74) *Attorney, Agent, or Firm* — Bose McKinney & Evans LLP (57) ABSTRACT

An inventive electrochemical sensor has a substrate with proximal and distal regions. The proximal region has at least one contact element configured to communicate with a measurement device. A working electrode is located in the distal region of the substrate and includes a conductive trace. A plurality of enzyme fields are provided, each enzyme field having an enzyme configured for providing a reaction with an analyte. The enzyme fields are spaced apart and each enzyme field is at least partially located on the conductive trace. The conductive trace may be provided in the form of a grid. The enzyme fields can be formed such that they extend beyond one or both edges of the trace or such that they cover only a portion of the full width of the trace. Manufacturing tolerances can be improved.

20 Claims, 2 Drawing Sheets

(56) References Cited

U.S. PATENT DOCUMENTS

| | | | |
|---|---|---|---|
| 5,437,999 A | 8/1995 | Diebold et al. | |
| 5,520,787 A | 5/1996 | Hanagan et al. | |
| 5,762,770 A | 6/1998 | Pritchard et al. | |
| 5,798,031 A | 8/1998 | Charlton et al. | |
| 6,129,823 A | 10/2000 | Hughes et al. | |
| 6,134,461 A | 10/2000 | Say et al. | |
| 6,360,888 B1 | 3/2002 | McIvor et al. | |
| 2004/0040866 A1* | 3/2004 | Miyashita | C12Q 1/004 |
| | | | 204/403.01 |
| 2005/0013731 A1 | 1/2005 | Burke et al. | |
| 2005/0016844 A1* | 1/2005 | Burke | G01N 33/558 |
| | | | 204/403.01 |
| 2005/0103624 A1 | 5/2005 | Bhullar et al. | |
| 2007/0246357 A1 | 10/2007 | Wu | |
| 2008/0242962 A1 | 10/2008 | Roesicke et al. | |
| 2010/0267161 A1* | 10/2010 | Wu | G01N 27/3274 |
| | | | 422/82.01 |
| 2011/0186428 A1* | 8/2011 | Beaty | G01N 27/327 |
| | | | 204/403.01 |
| 2011/0284393 A1 | 11/2011 | Macfie et al. | |
| 2012/0088993 A1 | 4/2012 | Buck et al. | |
| 2015/0257263 A1 | 9/2015 | Sethumadhavan et al. | |

FOREIGN PATENT DOCUMENTS

| | | |
|---|---|---|
| CN | 105466980 A | 4/2016 |
| CN | 106232901 A | 12/2016 |
| EP | 0 177 743 A2 | 4/1986 |
| EP | 2 774 538 A1 | 9/2014 |
| WO | WO 2005/032362 A2 | 4/2005 |
| WO | WO 2010/028708 A1 | 3/2010 |

OTHER PUBLICATIONS

International Search Report and Written Opinion of the International Searching Authority, PCT/EP2018/075031, dated Dec. 11, 2018, 12 pages.

Gao et al., Handbook of Functional Materials & Applications, China Machine Press, Jul. 31, 1991, pp. 869-874.

* cited by examiner

ELECTROCHEMICAL SENSOR AND SENSOR SYSTEM FOR DETECTING AT LEAST ONE ANALYTE

RELATED APPLICATIONS

This application is a continuation of PCT/EP2018/075031, filed Sep. 17, 2018, which claims priority to EP 17 191 602.6, filed Sep. 18, 2017, the entire disclosures of each of which are incorporated herein by reference.

BACKGROUND

This disclosure relates to an electrochemical sensor and a sensor system for electrochemically detecting at least one analyte in a sample of a body fluid as well as to a method for manufacturing the electrochemical sensor. The electrochemical sensor and the sensor system according to this disclosure may, primarily, be used for a long-term monitoring of an analyte concentration in a body fluid, in particular for a long-term monitoring of a glucose level or of the concentration of one or more other types of analytes in a body fluid. This disclosure may both be applied in the field of home care as well as in the field of professional care, such as in hospitals. However, other applications are feasible.

Monitoring certain body functions, more particularly monitoring one or more concentrations of certain analytes, plays an important role in the prevention and treatment of various diseases. Without restricting further possible applications, this disclosure is described in the following with reference to glucose monitoring in an interstitial fluid. However, this disclosure can also be applied to other types of analytes. Blood glucose monitoring may, specifically, be performed by using electrochemical sensors besides optical measurements. Examples of electrochemical sensors for measuring glucose, specifically in blood or other body fluids, are known from U.S. Pat. Nos. 5,413,690 A, 5,762,770 A, 5,798,031 A, 6,129,823 A or U.S. Publication No. 2005/0013731 A1.

In addition to "spot measurements" in which a sample of a body fluid is taken from a user, i.e., a human or an animal, in a targeted fashion and examined with respect to the analyte concentration, continuous measurements have become increasingly established. Thus, in the recent past, continuous measuring of glucose in the interstitial tissue, also referred to as "continuous glucose monitoring" or abbreviated to "CGM," has been established as another important method for managing, monitoring, and controlling a diabetes state. Herein, an active sensor region is applied directly to a measurement site which is, generally, arranged in an interstitial tissue, and may, for example, convert glucose into an amended entity by using an enzyme, in particular, glucose oxidase, generally abbreviated to "GOD." As a result, the detectable current may be related to the glucose concentration and can, thus, be used as a measurement variable. Examples of such transcutaneous measurement systems are described in U.S. Pat. No. 6,360,888 B1 or U.S. Publication No. 2008/0242962 A1.

Typically, current continuous monitoring systems are transcutaneous systems or subcutaneous systems. Accordingly, the actual electrochemical sensor or at least a measuring portion thereof may be arranged under the skin of the user. However, an evaluation and control part of the system, which may also be referred to as a "patch," may, generally, be located outside of the body of a user. Herein, the electrochemical sensor may, generally, be applied by using an insertion instrument, which is, in an exemplary fashion, described in U.S. Pat. No. 6,360,888 B1. However, other types of insertion instruments are also known. Further, a measurement device which may also acts as a control part may, typically, be required which may be located outside the body tissue and which has to be in communication with the electrochemical sensor. Generally, communication is established by providing at least one electrical contact between the electrochemical sensor and the measurement device, wherein the contact may be a permanent electrical contact or a releasable electrical contact. Other techniques for providing electrical contacts, such as by appropriate spring contacts, are generally known and may also be applied.

In continuous glucose measuring systems, the concentration of the analyte glucose may be determined by employing an electrochemical sensor comprising an electrochemical cell having at least a working electrode and a counter electrode. Herein, the working electrode may have a reagent layer comprising an enzyme with a redox active enzyme co-factor adapted to support an oxidation of the analyte in the body fluid. Further, the working electrode, usually, has a supporting layer of copper deposited on a substrate on which gold contacts are galvanically deposited. This kind of arrangement, however, lacks mechanical flexibility since bending the electrochemical sensor may easily result in a delamination of gold and copper from the substrate. As a result, the copper may become electrochemically accessible, whereby an oxidation current may be generated as a leakage current which may capable of influencing the measurement.

EP 0 177 743 A2 discloses an enzyme electrode comprising a carrier, an enzyme immobilized on a part of the outer surface of the carrier, a coating film consisting of a thin film permeable for a substrate for the enzyme and coating the portion where the enzyme is immobilized, and an internal electrode capable of applying voltage to the portion. A GOD electrode was prepared by using a mini-grid electrode as the internal electrode. For this purpose, a solution comprising GOD in a solvent was placed on a storage layer and the solvent was removed by evaporation. Thereafter, a gold mini-grid electrode was placed and fixed by a nylon net on the resulting storage layer. Further, GOD solution was placed on the gold mini-grid electrode through the nylon net and the solvent was made to evaporate, until, eventually, the gold mini-grid electrode was connected with a lead wire by means of a conductive bonding agent.

WO 2010/028708 A1 discloses an electrode system for measuring the concentration of an analyte under in-vivo conditions, comprising a counter-electrode having an electrical conductor, a working electrode having an electrical conductor on which an enzyme layer containing immobilized enzyme molecules for catalytic conversion of the analyte is arranged, and a diffusion barrier that slows the diffusion of the analyte from body fluid surrounding the electrode system to enzyme molecules down. This disclosure provides the enzyme layer in the form of multiple fields that are arranged on the conductor of the working electrode at a distance from each other. For this purpose, the working electrode is covered by an electrically insulating layer, wherein the multiple fields are arranged on top of openings formed by the electrically insulating layer.

Despite the advantages implied by the above-mentioned devices and methods known in the art, still, technical challenges remain, in particular, with regard to design and manufacturing of electrochemical sensors. Especially, the current design of the electrochemical sensors which are manufactured in accordance with the process as disclosed in WO 2010/028708 A1 requires that an enzyme paste is deposited very accurately into openings as comprised by an electrically insulating layer in order to thoroughly cover the electrically conducting surface of the working electrode.

SUMMARY

This disclosure teaches an electrochemical sensor and a sensor system for electrochemically detecting at least one analyte in a sample of a body fluid as well as a method for manufacturing the electrochemical sensor, which at least partially avoid the shortcomings of known devices and methods of this kind.

In particular, an electrochemical sensor is disclosed which, on one hand, may comprise a mechanically flexible sensor design while, on the other hand, may reduce manufacturing efforts in comparison to known manufacturing processes, specifically, with regard to an increase of the position tolerance.

As used in the following, the terms "have," "comprise" or "include" or any arbitrary grammatical variations thereof are used in a non-exclusive way. Thus, these terms may both refer to a situation in which, besides the feature introduced by these terms, no further features are present in the entity described in this context and to a situation in which one or more further features are present. As an example, the expressions "A has B," "A comprises B" and "A includes B" may both refer to a situation in which, besides B, no other element is present in A (i.e., a situation in which A solely and exclusively consists of B) and to a situation in which, besides B, one or more further elements are present in entity A, such as element C, elements C and D or even further elements.

Further, it shall be noted that the terms "at least one," "one or more" or similar expressions indicating that a feature or element may be present once or more than once typically will be used only once when introducing the respective feature or element. In the following, in most cases, when referring to the respective feature or element, the expressions "at least one" or "one or more" will not be repeated, non-withstanding the fact that the respective feature or element may be present once or more than once. It shall be understood for purposes of this disclosure and appended claims that, regardless of whether the phrases "one or more" or "at least one" precede an element or feature appearing in this disclosure or claims, such element or feature shall not receive a singular interpretation unless it is made explicit herein. By way of non-limiting example, the terms "enzyme field," "contact element," "electrode" and "conductive trace," to name just a few, should be interpreted wherever they appear in this disclosure and claims to mean "at least one" or "one or more" regardless of whether they are introduced with the expressions "at least one" or "one or more." All other terms used herein should be similarly interpreted unless it is made explicit that a singular interpretation is intended.

Further, as used in the following, the terms "preferably," "more preferably," "particularly," "more particularly," "specifically," "more specifically" or similar terms are used in conjunction with optional features, without restricting alternative possibilities. Thus, features introduced by these terms are optional features and are not intended to restrict the scope of the claims in any way. This disclosure may, as the skilled person will recognize, be performed by using alternative features. Similarly, features introduced by "in an embodiment of this disclosure" or similar expressions are intended to be optional features, without any restriction regarding alternative embodiments of this disclosure, without any restrictions regarding the scope of this disclosure and without any restriction regarding the possibility of combining the features introduced in such way with other optional or non-optional features of this disclosure.

As used herein, the term "sensor system," which may, alternatively, also be denoted by the term "sensor assembly," refers to a device which is configured for conducting at least one medical analysis. For this purpose, the sensor system may be a device configured for performing at least one diagnostic purpose and, specifically, comprising at least one analyte sensor for performing the at least one medical analysis. The sensor system may, specifically, comprise an assembly of two or more components capable of interacting with each other, such as in order to perform one or more diagnostic purposes, such as in order to perform the medical analysis. Specifically, the two or more components may be capable of performing at least one detection of the at least one analyte in the body fluid and/or in order to contribute to the at least one detection of the at least one analyte in the body fluid. As described below in more detail, the sensor system according to this disclosure comprises an assembly having at least one first component adapted for detecting at least one analyte in a sample of a body fluid, especially, by performing at least one measurement, at least one second component configured for performing at least one measurement in interoperation with the at least first component and for determining an analyte value in the sample of the body fluid by evaluating the at least one measurement, and at least one third component configured for providing interoperation between the at least one first component and the at least one second component.

As generally used, the terms "patient" and "user" may refer to a human being or an animal, independent from whether the human being or animal, respectively, may be in a healthy condition or may suffer from one or more diseases. As an example, the patient or the user may be a human being or an animal suffering from diabetes. However, additionally or alternatively, this disclosure may be applicable to other types of users, patients or diseases.

As further used herein, the term "body fluid" may, generally, refer to a fluid, in particular a liquid, which may typically be present in a body or a body tissue of the user or the patient and/or which may be produced by the body of the user or the patient. Preferably, the body fluid may be selected from the group consisting of blood and interstitial fluid. However, additionally or alternatively, one or more other types of body fluids may be used, such as saliva, tear fluid, urine or other body fluids. During the detection of the at least one analyte, the body fluid may be present within the body or body tissue. Thus, the sensor system may at least be configured for detecting the at least one analyte within the body tissue.

As further used herein, the term "analyte" may refer to an arbitrary element, component, or compound being present in the body fluid, wherein the presence and/or the concentration of the analyte may be of interest to the user, the patient, or to a medical staff, such as to a medical doctor. Particularly, the analyte may be or may comprise at least one arbitrary chemical substance or chemical compound which may participate in the metabolism of the user or the patient, such as at least one metabolite. As an example, the at least one analyte may be selected from the group consisting of glucose, cholesterol, triglycerides, lactate. Additionally or alternatively, however, other types of analytes may be used and/or any combination of analytes may be determined. The detection of the at least one analyte specifically may, in particular, be an analyte-specific detection. Without restricting further possible applications, this disclosure is described in the following with particular reference to a monitoring of glucose in an interstitial fluid. As generally used, at least one property of the analyte may be characterized by a "value" related to this property, such as a concentration, of the analyte. However, other kinds of properties may also be feasible, such as interfering substances or "interferents," i.e., additional redox active substances comprised by the body fluid which may be oxidized in a similar manner and may, thus, generate further electrons which may be detectable as an additional current.

In a first aspect of this disclosure, an electrochemical sensor for electrochemically detecting at least one analyte in a sample of a body fluid is disclosed. Accordingly, the electrochemical sensor comprises a substrate having a proximal region and a distal region, wherein the proximal region comprises at least one contact element which is configured to communicate with a measurement device, wherein the electrochemical sensor comprises at least one working electrode located in the distal region of the substrate and at least one counter electrode, wherein the working electrode has a plurality of enzyme fields, each enzyme field comprising at least one enzyme, the enzyme being configured for providing a reaction with the analyte, wherein the working electrode further comprises at least one conductive trace, wherein each of the enzyme fields is at least partially located on the conductive trace.

As used herein, the term "electrochemical sensor" refers to a sensor which is adapted for performing at least one electrochemical measurement, in particular a plurality or series of electrochemical measurements, in order to detect the at least one substance as comprised within the body fluid by using an amperometric method. Especially, the term "electrochemical measurement" refers to a detection of an electrochemically detectable property of the substance, such as an electrochemical detection reaction, by employing amperometric methods. Thus, for example, the electrochemical detection reaction may be detected by applying and comparing one or more electrode potentials. Specifically, the electrochemical sensor may be adapted to generate at least one electrical measurement signal which may directly or indirectly indicate a presence and/or an extent of the electrochemical detection reaction, such as at least one current signal and/or at least one voltage signal. The measurement may be a qualitative and/or a quantitative measurement. Still, other embodiments are feasible.

In a particularly preferred embodiment, the electrochemical sensor may be fully or a partially implantable and may, thus, be adapted for performing the detection of the analyte in the body fluid in a subcutaneous tissue, in particular, in an interstitial fluid. As used herein, the terms "implantable" or "subcutaneous" refer to being fully or at least partly arranged within the body tissue of the patient or the user. For this purpose, the electrochemical sensor may comprise an insertable portion, wherein the term "insertable portion" may generally refer to a part or component of an element configured to be insertable into an arbitrary body tissue while other parts or components may remain outside of the body tissue. Preferably, the insertable portion may fully or partially comprise a biocompatible surface, i.e., a surface which may have as little detrimental effects on the user, the patient, or the body tissue as possible, at least during typical durations of use. For this purpose, the insertable portion may be fully or partially covered with at least one biocompatible membrane, such as at least one polymer membrane or gel membrane which, on one hand, may be permeable for the body fluid or at least for the analyte as comprised therein and which, on the other hand, may retain sensor substances, such as one or more test chemicals within the electrochemical sensor, thus preventing a migration thereof into the body tissue.

Further, the electrochemical sensor comprises a substrate having a proximal region and a distal region, wherein the proximal region of the substrate comprises at least one contact element which is configured to communicate with the measurement device. As generally used, the term "contact element" (also referred to herein as simply "contact") refers to a unit which is configured for communication with the measurement device and which may, thus, comprise at least one electrical contact being adapted to provide an electrical contact with a corresponding electrical contact of the measurement device. However, other kinds of communication between the electrochemical sensor the measurement device may also be conceivable, in particular by using a contact element which may be adapted for wireless communication.

As generally used, the term "substrate" refers to an arbitrarily shaped body which is configured for carrying and/or supporting elements which are located on the substrate. For this purpose, the substrate may, preferably, comprise an electrically insulating material which can provide sufficient mechanical stability for the elements located on the substrate and, in addition, electrical insulation for electrodes and corresponding lead wires. Preferably, the substrate can be a flexible substrate which may, especially, comprise a bendable, electrically insulating material which may be biocompatible. Herein, the bendable and electrically insulating material may comprise at least one of polyimide (PI), polyethylene terephthalate (PET), polyethylene naphthalate (PEN), polypropylene (PP), polyamide (PA), flexible glass, or silicon. However, other electrically insulating and biocompatible materials may also be used as the substrate.

Preferably, the substrate refers to a three-dimensional form which predominantly extends in two directions, which are usually denoted by the terms "length" and "width," respectively, while the third direction, which is usually denoted by the term "height," is less pronounced. In particular, both the length and the width of the substrate exceed the height of the substrate by a factor of at least 5, preferably of at least 10, more preferred of at least 25. Moreover, the electrochemical sensor may be provided in form of a test element, in particular a test stripe, in which the length of the substrate may exceed the width of the substrate by a factor of at least 2, preferably of at least 5, more preferred of at least 10. However, other extensions of the substrate may also be feasible.

Further, the terms "proximal region" and "distal region" refer to respective partitions of the substrate, which can be assigned by either term by considering whether they carry and/or support the at least one contact element configured to communicate with the measurement device or not. As a result, the partition of the substrate, which carries and/or supports the at least one contact element configured to communicate with the measurement device, is denominated as the "proximal region," whereas the partition of the substrate, which carries and/or supports the at least one working electrode as described below in more detail, is denoted as the "distal region." Therefore, it can be feasible that the proximal region and the distal region are distinct regions on the substrate which respect to each other. However, it may also be possible that an overlap may exist between the proximal region and the distal region.

Further, the electrochemical sensor as used herein is arranged in a fashion of an electrochemical cell and, thus, employs at least one pair of electrodes. As generally used, the term "electrode" refers to a partition of the electrochemical sensor which is adapted to contact the body fluid, either directly or via at least one semipermeable membrane or layer. With regard to this disclosure, the at least one working electrode of the electrochemical sensor is located in the distal region of the substrate, thus, providing easier access for the electrodes to the body fluid. Further, each of the electrodes may be connected to at least one lead wire that may be configured for providing electrical connection between the respective electrode and the at least one contact element which is configured for providing interoperation between the electrochemical sensor and the measurement device. Further, at least one of the electrodes may be embodied in a fashion that an electrochemical reaction may occur at at least one surface of this electrode. In particular, this electrode may be embodied in a manner that oxidative processes and/or reductive processes may take place at selected surfaces of the electrode.

Thus, the at least one electrode pair as comprised by the electrochemical sensor has a working electrode and a counter electrode, wherein the working electrode further includes an enzyme, wherein the enzyme is configured for providing a reaction with the analyte while the counter electrode is maintained free from the enzyme. Herein, the substrate may comprise a front side and a backside, wherein the working electrode and the counter electrode may be located on the same side, i.e., the front side, of the substrate. In preferred alternative embodiment, while the working electrode may, still, be located on the front side of the substrate, the counter electrode may be located on the backside of the substrate. This particular embodiment may provide additional space on the front side for the working electrode, may generate a more homogeneous electrical field between the counter electrode and the working electrode, and may allow an easier manufacturing of the electrochemical sensor.

However, other embodiments having a different number of electrodes may also be feasible. In a particularly preferred embodiment, the electrochemical sensor may, additionally, comprise a reference electrode, wherein—in contrast to the working electrode—the reference electrode may, however, not include an enzyme. This arrangement may, especially, allow applying an electrical potential between the working electrode and the reference electrode and measuring a raw current generated hereby, preferably, between the working electrode and the counter electrode. Further, the reference electrode may, preferably, be located in the proximal region of the substrate, especially, on the front side of the substrate such as the working electrode.

Thus, the working electrode may include an enzyme, wherein the enzyme may be or comprise a test chemistry, while, if appropriate, the reference electrode and, preferably, the counter electrode maybe maintained free from the test chemistry. Generally, the term "test chemistry" refers to an arbitrary material or a composition of materials being adapted to change at least one detectable property in the presence of the at least one analyte, wherein the detectable property is selected here from the above-mentioned electrochemically detectable property. Specifically, the at least one test chemistry may be a highly selective test chemistry, which only changes the property if the analyte is present in the sample of the body fluid applied to the test element, whereas no change occurs if the analyte may not be present. More preferably, the degree or change of the at least one property may be dependent on the concentration of the analyte in the body fluid, in order to allow for a quantitative detection of the analyte. As used herein, the test chemistry may comprise one or more enzymes, in particular, glucose oxidase (GOD) and/or glucose dehydrogenase (GDH), preferably an enzyme which, by itself and/or in combination with other components of the detector substance, is adapted to perform an oxidative process or a reductive process with the at least one analyte to be detected. Additionally or alternatively, the test chemistry may comprise one or more auxiliary components, such as one or more co-enzymes and/or may comprise one or more catalysts and/or redox mediators. Additionally, the test chemistry may comprise one or more dyes, which, preferably in interaction with the one or more enzymes, may change their color in the presence of the at least one analyte to be detected.

According to this disclosure, the electrochemical sensor is arranged in form of a multiple field sensor. As a result, the working electrode comprises a plurality of enzyme fields, such as 2, 4, 6, 8, 9, 10, 12 or more enzyme fields. In contrast to a usual enzyme layer which is, typically, provided in a manner that it at least partially or, preferably, fully covers a surface of the working electrode which may be configured to contact the body fluid in form of a single continuous layer, the term "enzyme fields" refers to individual areas on the respective surface of the working electrode, wherein each of the individual areas which are configured to contact the body fluid comprises the enzyme but is located at a distance from each of adjacent enzyme fields. Herein, each of the enzyme fields comprises the at least one enzyme which is configured for providing a reaction with the analyte, wherein, the enzyme is provided in the same concentration for each of the enzyme fields. As a result of providing the same concentration, a more homogeneous electrical field can be generated within the working electrode.

Consequently, the enzyme fields may, preferably, be arranged side by side with respect of each other in a parallel manner on the respective surface of the working electrode, wherein adjacent enzyme fields are separated from each other by a gap which is maintained free from the enzyme. Preferably, adjacent enzyme fields may be spaced at least 3 mm, preferably at least 5 mm, distant from each other. As a result, a series of multiple individual enzyme fields of a single working electrode can be considered as a plurality of working electrodes arranged in series, thus, providing an improvement of a signal-to-noise ratio of the measurement signal.

In particular contrast to WO 2010/028708 A1 as cited above, wherein the working electrode is covered by an electrically insulating layer, wherein the multiple fields are arranged on top of openings as comprised by the electrically insulating layer, the working electrode in accordance with this disclosure further comprises at least one conductive trace, wherein each of the enzyme fields is at least partially located on the at least one conductive trace, in particular, on top of the at least one conductive trace. As used herein, the term "at least partially" refers to an arrangement in which a particular enzyme field may only cover a partition of the conductive trace or, as an alternative, in which the particular enzyme field may cover a partition of the conductive trace but, concurrently, also a further distinct part of the substrate apart from the conductive trace. For example, the particular enzyme field may extend beyond or project over the edge(s) of the trace. As generally used, the term "conductive trace" refers to at least one electrically conducting, preferably non-corrosive, especially biocompatible, material that is provided in form of an individual track which extends at least in the distal region of the substrate but may, preferentially, be connected to at least one lead wire or be continued as the at least one lead wire in the proximal region of the substrate, wherein the lead wire may be configured for providing electrical connection between the working electrode and the at least one contact element which is configured to communicate with the measurement device. Herein, the term "track" refers to a three-dimensional form of the trace which predominantly extends in one direction, which is usually denoted by the term "length," while the other two directions, which are usually denoted by the terms "width" and "height," respectively, are less pronounced. In particular, the length of the conductive trace may exceed both the width and the height of the conductive trace by a factor of at least 10, preferably of at least 50, more preferred of at least 100. Herein, the height of the conductive trace may, preferably, assume a thickness of 0.1-20 µm. Thus, in particular contrast to WO 2010/028708 A1 as cited above, position requirements are considerably reduced when the plurality of the enzyme fields are at least partially located on the at least one conductive trace.

In a particularly preferred embodiment, the working electrode comprises a multiplicity of conductive traces, thus, advantageously further reducing the position requirements during placement of the plurality of the enzyme fields. Herein, the multiplicity of the conductive traces may be provided in an arbitrary manner, however, providing the multiplicity of conductive traces in form of a grid may, especially, be preferred. However, other kinds of arrangements may also be feasible. As generally used, the term "grid" implies a regular arrangement in which distances between adjacent conductive traces are selected from a single value or from a small interval of deviations compared to the distance, such as less than 10%, preferably less than 5%, of the distance. As a further advantage, placing the multiplicity of the conductive traces in form of a grid may, further, simplify the manufacturing of the working electrode.

In a further, particularly preferred embodiment, the non-corrosive, electrically conducting material as used for the at least one conductive trace may comprise gold which is known to be easily deposited, thus, further simplifying the manufacturing of the working electrode. In order to further facilitate a deposition of the electrically conducting material, at least one non-corrosive bonding agent, may, in particular, be used in addition to the gold. Preferably, the bonding agent may be selected from at least one of titanium or palladium, both of which are known to be suited for this purpose, wherein a layer having a thickness of 1-100 nm, preferably of 10-50 nm, may, especially, be appropriate, on which the non-corrosive, electrically conducting material, in particular, the gold, may be located. Herein, the bonding agent may, especially, be used for enhancing adhesion of the electrically conducting material on the surface of the substrate. Thus, this bonding agent may also be used for the other electrodes located on the substrate. However, other kinds of non-corrosive, electrically conducting materials and/or bonding agents may also be conceived.

In a particular embodiment, the conductive trace can comprise a first partition and a second partition, wherein the first partition may be located in the distal region while the second partition may be located in the proximal region. As indicated above, the second partition of the conductive trace located in the proximal region can, thus, be considered as being continued as the at least one lead wire of the working electrode in the proximal region of the substrate which is configured for providing electrical connection between the working electrode and the at least one contact element. This kind of arrangement may, as an alternative view, also be considered as overlap between the first partition and the second partition of the conductive trace. Since copper is known as a corrosive material upon exposure to the body fluid, causing the copper to oxidize, thus, gradually changing bright copper surfaces to tarnish, it is preferred in this particular embodiment that the at least the first partition of the conductive trace may be devoid of copper while the second partition of the conductive trace may, still, comprise copper as one of the electrically conducting material or the bonding agent for a further electrically conducting material. As a result, the at least one lead wire which may comprise copper in the proximate region may, especially, profit from an enhanced mechanical stability of copper traces compared to gold traces.

In a further embodiment, the substrate may be partially covered by a solder resist in a manner that the solder resist at least partially covers the proximal region of the substrate. Herein, the solder resist may, preferably, partially cover the substrate in a manner that the distal region of the substrate is devoid of the solder resist. As generally used, the term "solder resist" refers to a thin lacquer-like layer of polymer usually applied to conductive traces, such as in a printed circuit board (PCB), in order to, on one hand, provide a protection against oxidation and, on the other hand, to avoid forming of solder bridges between adjacent solder pads. Since it is preferred in the particular embodiment as described above that the at least the first partition of the conductive trace which is located in the distal region of the substrate may be devoid of copper, it may, preferably, be possible to provide the electrochemical sensor without a solder resist within the distal region of the substrate, thus, allowing the sample of the body fluid to better contact the plurality of the enzyme fields, whereas the solder resist may be advantageous in an embodiment in which the second partition of the conductive trace which is located in the proximal region of the substrate may comprise copper.

In a particularly preferred embodiment, the electrochemical sensor may comprise a three-electrode arrangement as described in the following. Herein, the working electrode may have a test chemistry which comprises carbon paste having carbon particles and a polymer binder as a conductive substance, manganese dioxide ($MnO_2$), preferably in particulate form, as a catalyst and/or a mediator, and at least one of the enzymes glucose oxidase (GOD) or glucose dehydrogenase (GDH) which may be applied to a surface of a polyimide substrate in form of a plurality of enzyme fields. Further, the working electrode may, in addition, have a multiplicity of conductive traces in form of a grid, wherein the conductive traces may comprise gold, which may be located on a layer of at least one of titanium or palladium acting as non-corrosive bonding agent. For sake of increasing mechanical stability of the electrochemical sensor, the conductive traces in the proximal reason may comprise copper as electrically conducting material or bonding agent. In order to achieve protection from copper oxidation, a solder resist may cover the proximal region of the substrate. In accordance with this disclosure, each of the enzyme fields is at least partially located on the multiplicity of the conductive traces, thereby, in particular, contributing to a simplified manufacturing of the electrochemical sensor. Further, the counter electrode may be or comprise a gold electrode while the reference electrode may be or comprise an Ag/AgCl electrode, wherein both electrodes are maintained free from the enzyme. The three-electrode arrangement as described herein may, thus, allow applying an electrical potential between the working electrode and the reference electrode and measuring the raw current generated hereby, preferably, between the working electrode and the counter electrode. Further, the substrate comprises a front side and a backside, wherein the working electrode and the reference electrode may be located on the front side of the substrate, while the counter electrode may be located on the backside of the substrate.

Based on the at least one measurement signal, the measurement device may generate an additional value related to the measurement signal. As generally used, a sensitivity S of the electrochemical sensor may, thus, be obtained by measuring a raw current I as the measurement signal using the electrochemical sensor, an taking into account a concentration c of the analyte, such as the glucose. In an ideal representation, the sensitivity S of the electrochemical sensor may, generally, be defined by Equation (1):

$$S=(I-I_0)/c, \quad (1)$$

wherein the term Io refers to a possible zero current, which may originate from interferents being present in the body fluid. In case of a sensitivity drift, the raw current I may, thus, be measured and the sensitivity S may, subsequently, be corrected. In practice, Equation (1) is empirically known to hold true for a glucose concentration up to 100 mg/dl to 150 mg/dl whereas a more complex behavior appears for higher concentrations.

In a further aspect, a method for manufacturing an electrochemical sensor, in particular an electrochemical sensor as described elsewhere in this document, is disclosed. Herein, the method comprises the indicated steps a) to c) which may, preferably, be performed in the given order, starting with step a). However, steps b) and c) may also be performed in a different order or at least partially concurrently. Accordingly, the method comprises the following steps:

a) providing a substrate having a proximal region and a distal region, wherein the proximal region comprises at least one contact element which is configured to communicate with a measurement device;

b) placing at least one conductive trace in the distal region of the substrate and generating at least one working electrode by placing a plurality of enzyme fields on the conductive trace, wherein each enzyme field comprises at least one enzyme, the enzyme being configured for providing a reaction with the analyte;

c) placing at least one counter electrode on the substrate; and d) providing respective electrical connection from each of the conductive trace and the counter electrode to the contact element.

In addition, further electrodes, in particular at least one reference electrode, may, be placed on the substrate, wherein electrical connection to the contact element may also be provided.

In a particularly preferred embodiment, placing the at least one conductive trace may comprise printing a first preparation comprising at least one non-corrosive, electrically conducting material, preferably gold, and, preferably, a volatile solvent on a position which may be intended for this purpose on the substrate. Herein, the printing may be performed in a manner that the layer of the non-corrosive, electrically conducting material may assume a thickness of 0.1-1.0 µm. Preferably, the layer of the non-corrosive, electrically conducting material may be printed on an additional layer comprising at least one non-corrosive bonding agent, especially, selected from at least one of titanium or palladium, having a thickness of 1-10 nm, preferably of 2-5 nm, in order to enhance adhesion of the layer of the non-corrosive, electrically conducting material, in particular the gold, on the substrate.

Similarly, in a further particularly preferred embodiment, placing the plurality of enzyme fields on the conductive trace may comprise printing a second preparation comprising glucose oxidase and/or glucose dehydrogenase as the enzyme, manganese dioxide as the catalyst, carbon particles, and a polymer binder, on the positions which may be intended for this purpose at least partially on the at least one conductive trace.

For further details concerning the method, reference may be made to the description of the electrochemical sensor as provided elsewhere in this document.

In a further aspect, a sensor system for electrochemically detecting at least one analyte in a sample of a body fluid disclosed. Accordingly, the sensor system comprises an assembly having at least one electrochemical sensor as described elsewhere in this document as at least one first component, a measurement device as a second component and at least one contact element configured for providing interoperation between the at least one electrochemical sensor and the measurement device as a third component. Herein, the measurement device is, on one hand, configured for performing at least one electrical measurement in interoperation with the at least one electrochemical sensor and, on the other hand, for determining an analyte value in the sample of the body fluid by evaluating the at least one electrical measurement.

As used herein, the term "measurement device" refers to an arbitrary device which can be handled independently from the electrochemical sensor. The measurement device may, especially, be configured to perform the at least one amperometric measurement by using the electrodes of the electrochemical sensor, in particular, to detect at least one direct current signal and at least one current response, preferably, concurrently or subsequently. For this purpose, the measurement device may, preferably, be adapted for applying an electrical potential between the at least one working electrode and the at least one reference electrode of the electrochemical sensor and for measuring a raw current generated hereby, preferably, between the working electrode and the at least one counter electrode of the electrochemical sensor. However, other embodiments may also be feasible.

Further, the measurement device may be configured to derive at least one item of information regarding an analyte value related to the analyte in the sample of the body fluid from this detection. For this purpose, the measurement device may comprise at least one electronic evaluation device interacting with the electrochemical sensor, in particular, in order to derive the at least one analyte value from the at least one signal. Thus, the electronics unit may comprise at least one evaluation device comprising at least one data processing device, such as one or more of a microcontroller, an application-specific integrated circuit (ASIC), a Field-Programmable Gate Array (FPGA). However, other kinds of devices may also be feasible.

In a further aspect, a sensor system for electrochemically detecting at least one analyte in a sample of a body fluid is disclosed. The sensor system comprises at least one electrochemical sensor as described above or as will further be described below in more detail. Further, the sensor system comprises a measurement device and at least one sensor system contact element configured for providing interoperation between the electrochemical sensor and the measurement device. The measurement device is, in interoperation with the electrochemical sensor, configured for performing at least one electrical measurement, and the measurement device is further configured for determining an analyte value in the sample of the body fluid by evaluating the electrical measurement.

The sensor system contact element may correspond to the contact element of the electrochemical sensor. Thus, the sensor system contact element may be the contact element of the electrochemical sensor. However, other embodiments may also be feasible. Thus, the contact element and the sensor system contact element may be separate contact elements. Further, the sensor system contact element may form part of the electrochemical sensor.

The electrochemical sensor and the sensor system as well as the method for manufacturing the electrochemical sensor according to this disclosure exhibit a number of advantages with respect to known methods and devices. In contrast thereto, the present method may, on one hand, allow providing a simplified sensor design while, on the other hand, the manufacturing efforts can, significantly, be reduced in comparison to known manufacturing processes, specifically, since they allow increasing the position tolerance of the enzyme fields by placing the enzyme fields on a conductive trace or on a grid formed by a plurality of conductive traces, whereby a noticeable simplification of the manufacturing process can be achieved.

This manufacturing process is in further contrast to known electrochemical sensors that comprise an arrangement in which the working electrode has a supporting layer of copper deposited on a substrate on which gold contacts are deposited. In contrast, the arrangement according to this disclosure comprises mechanical flexibility since bending the electrochemical sensor may not result in a delamination of the conductive traces and the enzyme fields from the substrate, whereby leakage currents which may influence the measurement can be avoided.

Summarizing, the following embodiments are contemplated. Other embodiments may, however, also be feasible.

Embodiment 1: An electrochemical sensor for electrochemically detecting at least one analyte in a sample of a body fluid, wherein the electrochemical sensor comprises a substrate having a proximal region and a distal region, wherein the proximal region comprises at least one contact element which is configured to communicate with a measurement device, wherein the electrochemical sensor comprises at least one working electrode located in the distal region of the substrate and at least one counter electrode, wherein the working electrode has a plurality of enzyme fields, each enzyme field comprising at least one enzyme, the enzyme being configured for providing a reaction with the analyte, wherein the working electrode further comprises at least one conductive trace, wherein each of the enzyme fields is at least partially located on the conductive trace.

Embodiment 2: The electrochemical sensor according to the preceding Embodiment, wherein the working electrode comprises a multiplicity of conductive traces.

Embodiment 3: The electrochemical sensor according to the preceding Embodiment, wherein the multiplicity of the conductive traces forms a grid.

Embodiment 4: The electrochemical sensor according to any one of the preceding Embodiments, wherein the conductive trace comprises at least one non-corrosive, electrically conducting material.

Embodiment 5: The electrochemical sensor according to the preceding Embodiment, wherein the non-corrosive, electrically conducting material comprises gold.

Embodiment 6: The electrochemical sensor according to any one of the preceding Embodiments, wherein the conductive trace is located on a layer comprising at least one non-corrosive bonding agent, wherein the layer comprising the non-corrosive bonding agent is located on the substrate.

Embodiment 7: The electrochemical sensor according to the preceding Embodiment, wherein the non-corrosive bonding agent is selected from at least one of titanium or palladium.

Embodiment 8: The electrochemical sensor according to any one of the preceding Embodiments, wherein the conductive trace is provided in form of an individual track extending at least in the distal region of the substrate.

Embodiment 9: The electrochemical sensor according to any one of the preceding Embodiments, wherein the conductive trace predominantly extends in one direction denoted as a length, while the other two directions denoted as a width and a height, respectively, are less pronounced.

Embodiment 10: The electrochemical sensor according to the preceding Embodiment, wherein the length of the conductive trace exceeds both the width and the height of the conductive trace by a factor of at least 10, preferably of at least 50, more preferred of at least 100.

Embodiment 11: The electrochemical sensor according to any one of the preceding Embodiments, wherein the conductive trace is connected to at least one lead wire in the proximal region of the substrate or wherein the conductive trace is continued as the at least one lead wire in the proximal region of the substrate.

Embodiment 12: The electrochemical sensor according to the preceding Embodiment, wherein the lead wire is configured for providing electrical connection between the working electrode and the at least one contact element configured to communicate with the measurement device.

Embodiment 13: The electrochemical sensor according to any one of the preceding Embodiments, wherein the conductive trace comprises a first partition located in the distal region and a second partition located in the proximal region.

Embodiment 14: The electrochemical sensor according to the preceding Embodiment, wherein at least the first partition of the conductive trace is devoid of copper.

Embodiment 15: The electrochemical sensor according to the preceding Embodiment, wherein the second partition of the conductive trace comprises copper as one of the electrically conducting material or the bonding agent for a further electrically conducting material.

Embodiment 16: The electrochemical sensor according to any one of the preceding Embodiments, wherein the substrate is partially covered by a solder resist.

Embodiment 17: The electrochemical sensor according to the preceding Embodiment, wherein the solder resist at least partially covers the proximal region of the substrate.

Embodiment 18: The electrochemical sensor according to any one of the two preceding Embodiments, wherein the distal region of the substrate is devoid of the solder resist.

Embodiment 19: The electrochemical sensor according to any one of the preceding Embodiments, wherein the substrate is a flexible substrate comprising a bendable electrically insulating material.

Embodiment 20: The electrochemical sensor according to any one of the preceding Embodiments, wherein the bendable electrically insulating material comprises at least one of polyimide (PI), polyethylene terephthalate (PET), polyethylene naphthalate (PEN), polypropylene (PP), polyamide (PA), flexible glass, or silicon.

Embodiment 21: The electrochemical sensor according to any one of the preceding Embodiments, wherein the substrate further comprises a front side and a backside.

Embodiment 22: The electrochemical sensor according to the preceding Embodiment, wherein the working electrode is located on the front side of the substrate.

Embodiment 23: The electrochemical sensor according to any one of the two preceding Embodiments, wherein the counter electrode is located in one of the front side or the backside of the substrate.

Embodiment 24: The electrochemical sensor according to any one of the preceding Embodiments, wherein the substrate predominantly extends in two directions denoted as length and width, respectively, while the third direction denoted as height is less pronounced.

Embodiment 25: The electrochemical sensor according to the preceding Embodiment, wherein both the length and the width of the substrate exceed the height of the substrate by a factor of at least 5, preferably of at least 10, more preferred of at least 25.

Embodiment 26: The electrochemical sensor according to any one of the two preceding Embodiment, wherein the electrochemical sensor is provided in form of a test element, in particular a test strip.

Embodiment 27: The electrochemical sensor according to the preceding Embodiment, wherein, the length of the substrate exceeds the width of the substrate by a factor of at least 2, preferably of at least 5, more preferred of at least 10.

Embodiment 28: The electrochemical sensor according to any one of the preceding Embodiments, wherein the electrochemical sensor is arranged in form of a multiple field sensor.

Embodiment 29: The electrochemical sensor according to the preceding Embodiment, wherein the working electrode comprises a plurality of enzyme fields, preferably, 2, 4, 6, 8, 9, 10, 12 or more enzyme fields.

Embodiment 30: The electrochemical sensor according to any one of the two preceding Embodiments, wherein each of the enzyme fields refer to an individual area arranged side by side with respect of each other in a parallel manner on a respective surface of the working electrode, wherein each of the individual areas comprises the enzyme.

Embodiment 31: The electrochemical sensor according to the preceding Embodiment, wherein the enzyme is provided in the same concentration for each of the enzyme fields.

Embodiment 32: The electrochemical sensor according to any one of the two preceding Embodiments, wherein each of the individual areas is located at a distance from each of adjacent enzyme fields.

Embodiment 33: The electrochemical sensor according to the preceding Embodiment, wherein adjacent enzyme fields are separated from each other by a gap which is maintained free from the enzyme.

Embodiment 34: The electrochemical sensor according to any one of the two preceding Embodiments, wherein adjacent enzyme fields are spaced at least 3 mm, preferably at least 5 mm, distant from each other.

Embodiment 35: The electrochemical sensor according to any one of the preceding Embodiments, wherein the electrochemical sensor further comprises at least one reference electrode.

Embodiment 36: The electrochemical sensor according to the preceding Embodiment, wherein the reference electrode is located in the proximal region of the substrate.

Embodiment 37: The electrochemical sensor according to any one of the preceding Embodiments, wherein the electrochemical sensor is a fully implantable sensor or a partially implantable sensor.

Embodiment 38: The electrochemical sensor according to any one of the preceding Embodiments, wherein the electrochemical sensor is configured for continuously monitoring an analyte, preferably in a subcutaneous tissue.

Embodiment 39: The electrochemical sensor according to any one of the preceding Embodiments, wherein the electrochemical sensor is configured for a continuous measurement of the analyte in a body fluid, preferably in an interstitial fluid.

Embodiment 40: The electrochemical sensor according to any one of the preceding Embodiments, wherein the electrochemical sensor is configured for a continuous measurement of the analyte in blood.

Embodiment 41: The electrochemical sensor according to any one of the preceding Embodiments, wherein the analyte comprises glucose.

Embodiment 42: The electrochemical sensor according to the preceding Embodiment, wherein the enzyme is one of glucose oxidase (GOD) or glucose dehydrogenase (GODH).

Embodiment 43: The electrochemical sensor according to any one of the preceding Embodiments, wherein the enzyme is provided in form of an enzyme paste.

Embodiment 44: The electrochemical sensor according to the preceding Embodiment, wherein the enzyme paste further comprises manganese dioxide as a catalyst, carbon particles, and a polymer binder.

Embodiment 45: A method for manufacturing an electrochemical sensor, comprising the steps:
  a) providing a substrate having a proximal region and a distal region, wherein the proximal region comprises at least one contact element which is configured to communicate with a measurement device;
  b) placing at least one conductive trace in the distal region of the substrate and generating at least one working electrode by placing a plurality of enzyme fields on the conductive trace, wherein each enzyme field comprises at least one enzyme, the enzyme being configured for providing a reaction with the analyte;
  c) placing at least one counter electrode on the substrate; and
  d) providing respective electrical connection from each of the conductive trace and the counter electrode to the contact element.

Embodiment 46: The method according to the preceding Embodiment, wherein the method is configured for manufacturing an electrochemical sensor according to any one of the preceding Embodiments referring to an electrochemical sensor.

Embodiment 47: The method according to any one of the preceding Embodiments referring to a method, the method further comprising the following step:
  e) placing at least one reference electrode in the proximal region of on the substrate and providing electrical connection to the contact element.

Embodiment 48: A sensor system for electrochemically detecting at least one analyte in a sample of a body fluid, the sensor system comprising at least one electrochemical sensor according to any one of the preceding Embodiments referring to an electrochemical sensor, a measurement device and at least one contact element configured for providing interoperation between the electrochemical sensor and the measurement device, wherein the measurement device is, in interoperation with the electrochemical sensor, configured for performing at least one electrical measurement, and wherein the measurement device is further configured for determining an analyte value in the sample of the body fluid by evaluating the electrical measurement.

Embodiment 49: The sensor system according to the preceding Embodiment, wherein the measurement device is configured to be handled independently from the electrochemical sensor.

Embodiment 50: The sensor system according to any one of the preceding Embodiments referring to a sensor system, wherein the measurement device is configured for applying an electrical potential between the at least one working electrode and the at least one reference electrode of the electrochemical sensor and for measuring a raw current generated hereby, preferably, between the working electrode and the at least one counter electrode of the electrochemical sensor.

Embodiment 51: The sensor system according to any one of the preceding Embodiments referring to a sensor system, wherein the measurement device is, further, configured for deriving at least one item of information regarding an analyte value related to the analyte in the sample of the body fluid from this detection.

Embodiment 52: A sensor system for electrochemically detecting at least one analyte in a sample of a body fluid, the sensor system comprising at least one electrochemical sensor according to any one of the preceding embodiments referring to an electrochemical sensor, a measurement device and at least one sensor system contact element configured for providing interoperation between the electrochemical sensor and the measurement device, wherein the measurement device is, in interoperation with the electrochemical sensor, configured for performing at least one electrical measurement, and wherein the measurement device is further configured for determining an analyte value in the sample of the body fluid by evaluating the electrical measurement.

Embodiment 53: The sensor system according to the preceding embodiment, wherein the sensor system contact element corresponds to the contact element of the electrochemical sensor.

Embodiment 54: The sensor system according to any one of the two preceding embodiments, wherein the sensor system contact element forms part of the electrochemical sensor.

BRIEF DESCRIPTION OF THE DRAWINGS

The above-mentioned aspects of exemplary embodiments will become more apparent and will be better understood by reference to the following description of the embodiments taken in conjunction with the accompanying drawings, wherein.

DESCRIPTION

The embodiments described below are not intended to be exhaustive or to limit the invention to the precise forms disclosed in the following detailed description. Rather, the embodiments are chosen and described so that others skilled in the art may appreciate and understand the principles and practices of this disclosure.

Figure 1:
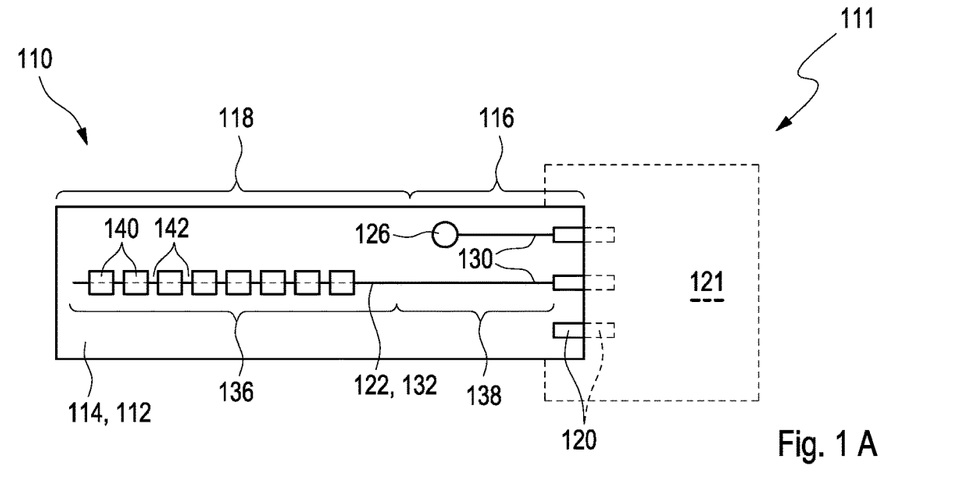
FIGS. 1A-1D schematically illustrate a first embodiment of an electrochemical sensor for electrochemically detecting at least one analyte in a sample of a body fluid according to this disclosure in a top view (FIG. 1A), a back view (FIG. 1B) and two profiles (FIGS. 1C and 1D)

FIG. 1 schematically illustrates a first, particularly preferred embodiment of an electrochemical sensor 110 for electrochemically detecting at least one analyte in a sample of a body fluid, wherein the electrochemical sensor 110 constitutes a part of a sensor system 111 which is configured for electrochemically detecting at least one analyte in a sample of a body fluid.

FIG. 1A illustrates the electrochemical sensor 110 and the sensor system 111 in a top view showing a front side 112 of a substrate 114 comprised by the electrochemical sensor 110. In this particular embodiment, the substrate 114 is a flexible substrate, thus, comprising a biocompatible bendable, electrically insulating material, in particular, a polyimide. However, other flexible biocompatible materials may also be feasible. Herein, the substrate 114 has a proximal region 116 and a distal region 118, wherein the proximal region is configured to carry and/or support contact elements 120 (also referred to herein as "contacts") which are adapted to communicate with a measurement device, which is schematically depicted here using the reference sign 121, that can be handled independently from the electrochemical sensor 110 and which may be configured in a manner to perform at least one amperometric measurement by using the electrochemical sensor 110 and to derive at least one item of information regarding an analyte value related to the analyte in the sample of the body fluid from this at least one measurement.

As schematically depicted in FIG. 1A, the contact elements 120 may be provided in form of a plurality of electrical contacts which are configured to provide electrical contact with corresponding electrical contacts of the measurement device 121. However, one or more contact elements 120 which may be adapted for wireless communication with the measurement device 121 may also be feasible. Thus, while a partition of the substrate 114 which may be configured to carry and/or support the contact elements 120 is denoted as the proximal region 116, a further partition of the substrate 114, which may be configured to carry and/or support a working electrode 122 as described below in more detail is denominated as the distal region 118. As schematically shown in FIG. 1A, the proximal region 116 and the distal region 118 may be provided as two distinct regions on the substrate 114, wherein it may, however, also be possible that an overlap may exist between the proximal region 116 and the distal region 118.

In the particular embodiment of FIG. 1, the electrochemical sensor 110 has a three-electrode arrangement comprising the working electrode 122, a counter electrode 124, and a reference electrode 126. Herein, the distal region 118 of the substrate 114 comprises the working electrode 122, while a counter electrode 124 may extend over both the distal region 118 and the proximal region 116, whereas the reference electrode 126 may be located in the proximal region 116 of the substrate 114. Further, both the working electrode 122 and the reference electrode 126 may, as depicted in FIG. 1A, be located on the front side 112 of the substrate 114 while the counter electrode 124 may, as shown in FIG. 1B, be located on a backside 128 of the substrate 114. Herein, each of the electrodes 122, 124, 126 are connected to the contact elements 120 by a lead wire 130 configured for providing electrical connection between the respective electrode 122, 124, 126 and the at least one corresponding contact element 120.

As schematically depicted in FIG. 1A, the working electrode 122 comprises a conductive trace 132, wherein, in this particular embodiment, the conductive trace 132 comprises gold as a non-corrosive, electrically conducting material. As can be seen in FIGS. 1C and 1D, the conductive trace 132 may, additionally, comprise a thin layer 134 of titanium as a non-corrosive bonding agent, thus, improving adhesion between the conductive trace 132 and the substrate 114. As an alternative, palladium may also be used as the non-corrosive bonding agent. As schematically depicted in FIG. 1A, the conductive trace 132 may, preferably, assume a three-dimensional form which predominantly extends in one direction usually denoted as length of the conductive trace 132, while the other two directions are usually denoted as width and height of the conductive trace 132, respectively, and are less pronounced. In particular, the length of the conductive trace 132 may exceed both the width and the height of the conductive trace 132 by a factor of at least 10, preferably of at least 50, more preferred of at least 100.

In particular, the conductive trace 132 may comprise a first partition 136 located in the distal region 118 and a second partition 138 located in the proximal region 116 of the substrate 114. Herein, the second partition 138 of the conductive trace 132 which is located in the proximal region 116 of the substrate 114, can thus be considered as being continued as the lead wire 130 connecting the working electrode 122 with the at least one corresponding contact element 120. In this particularly preferred embodiment of the electrochemical sensor 110, at least the first partition 136 of the conductive trace 132 is devoid of copper whereas the second partition 138 of the conductive trace 134 may comprise copper as an electrically conducting material or as a bonding agent for a further electrically conducting material, especially, in order to provide increased mechanical stability to the lead wire 130.

Further, the working electrode has a plurality of enzyme fields 140, wherein each enzyme field 140 comprises a test chemistry having at least one enzyme, in particular, glucose oxidase (GOD) and/or glucose dehydrogenase (GDH). As a result, the enzyme is, by itself and/or in combination with other components, configured for providing a reaction with the analyte. Further, the test chemistry may comprise one or more auxiliary components, in particular, a carbon paste having carbon particles and a polymer binder as a conductive substance and manganese dioxide ($MnO_2$), preferably in particulate form, as a catalyst and/or a mediator. According to this disclosure, each of the enzyme fields 140 is located on the substrate 114 in a manner that it at least partially covers the conductive trace 132.

As schematically depicted in FIG. 1A, the working electrode 122 comprises 8 enzyme fields 140 which are arranged side by side with respect of each other, thereby forming a series of enzyme fields 140. However, other kinds of arrangements are also feasible, such as 2, 4, 6, 8, 9, 12, 15, 16, 20, 24, 25, 32 or more enzyme fields which may be arranged in the same or in a different manner as long as they at least partially cover the conductive trace 132. As a result, adjacent enzyme fields may be separated from each other by a gap 142 which is maintained free of the enzyme. Preferably, the gap 142 between adjacent enzyme fields may assume at least 3 mm, preferably at least 5 mm. Consequently, the series of the multiple individual enzyme fields 140 can be considered as a plurality of working electrodes 122 arranged in series, thus, being capable of improving a signal-to-noise ratio of the measurement signal. Thus, in particular contrast to WO 2010/028708 A1 as cited above, position requirements are considerably reduced when the plurality of the enzyme fields 140 are at least partially located on the conductive trace 132.

Further, FIGS. 1C and 1D schematically illustrate two profiles of the electrochemical sensor 110 which are not to scale. Herein, the side view as depicted in FIG. 1C shows a first profile 144 through the substrate 114 in the distal region 118 at a location at which the substrate 114 carries the conductive trace 132 whereas FIG. 1D depicts a second profile 146 through the substrate 114 in the proximal region 116, again, at a location at which the substrate 114 carries the conductive trace 132. In this exemplary embodiment, the substrate 114 having a thickness of 100 µm is covered on both sides by the thin layer 134 of titanium having a thickness of 1-10 nm, preferably of 2-5 nm, as the non-corrosive bonding agent. Further, on the backside 128 of the substrate 114 the counter electrode 124 is located on the titanium layer 134 while on the front side 112 of the substrate 114 the conductive trace 132 as part of the working electrode 122 is located on the titanium layer 134. Herein, both the counter electrode 124 and the conductive trace 132 of the working electrode 122 may have a thickness of 0.1-1.0 µm, such as 0.5 µm. As already indicated above, the working electrode 122 further comprises the plurality of the enzyme fields 140 which are arranged side by side with respect of each other in a manner that they at least partially cover the conductive trace 132, whereby adjacent enzyme fields 140 are separated from each other by the gap 142 which is maintained free from the enzyme.

As can be derived from the second profile 146 as shown in FIG. 1D, the substrate 114 is, preferably, covered by a solder resist 148 in the proximal region of the substrate. Herein, the solder resist 148 comprises a lacquer-like layer of polymer having a thickness of 10-15 µm, which is applied here, on one hand, to provide a protection against oxidation, and, on the other hand, to avoid forming of solder bridges between adjacent electrically conducting areas. In contrast hereto, the distal region 118 of the substrate 114, preferably, remains devoid of the solder resist 148. This arrangement as schematically depicted in FIG. 1C is possible since, as described above, the first partition 136 of the conductive trace 132 which is located in the distal region 118 of the substrate 114 in the exemplary embodiment of FIG. 1 comprises gold as a non-corrosive, electrically conducting material but is devoid of copper, thereby removing a potential source of oxidation. As a result, providing the electrochemical sensor 110 without the solder resist 148 within the distal region 118 of the substrate 114, thus, allows the sample of the body fluid to better contact the plurality of the enzyme fields 140, whereas the solder resist 148 may be advantageous in the second partition 138 of the conductive trace 132 which is located in the proximal region 116 of the substrate 114 that may comprise copper in order to achieve an increased mechanical stability.

Figure 2:
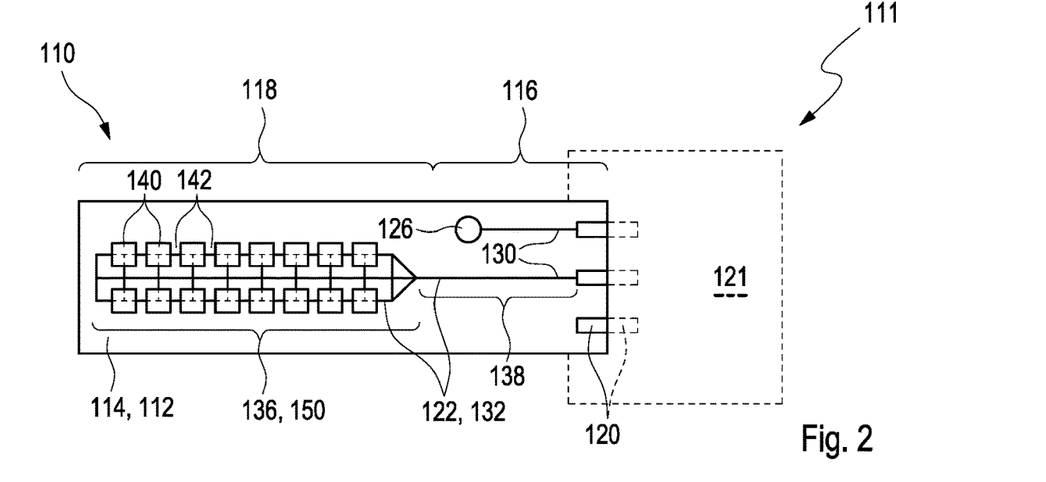
FIG. 2 schematically illustrates a further embodiment of the electrochemical sensor according to this disclosure in a top view.

In a further, particularly preferred embodiment of the electrochemical sensor 110 and the sensor system 111 as illustrated in FIG. 2 which presents the front side 112 of the substrate 114 of the electrochemical sensor 110, the working electrode 122 comprises a multiplicity of conductive traces 132. As a particular advantage, the position requirements during placement of the plurality of the enzyme fields 140 may, thus, further be reduced. In general, the multiplicity of the conductive traces 132 may be provided in an arbitrary manner, however, as depicted in FIG. 2, the multiplicity of conductive traces 132 may, as particularly be preferred, provided in form of a grid 150. However, other kinds of arrangements may also be feasible. As a result, a regular arrangement of the multiplicity of the conductive traces 132 in which the gaps 142 between adjacent conductive traces 132 may be selected from a single value or from a small interval of deviations compared to the distance, such as less than 10%, preferably less than 5%, of the distance. As can be seen from FIG. 2, placing the multiplicity of the conductive traces 132 in form of the grid 150 can, further, simplify the manufacturing of the working electrode 122.

For a presentation of the backside 128 and the profiled 144, 146 of the further, particularly preferred embodiment of the electrochemical sensor 110 as illustrated in FIG. 2, reference may be made to FIGS. 1B to 1D, respectively.

Figure 3:
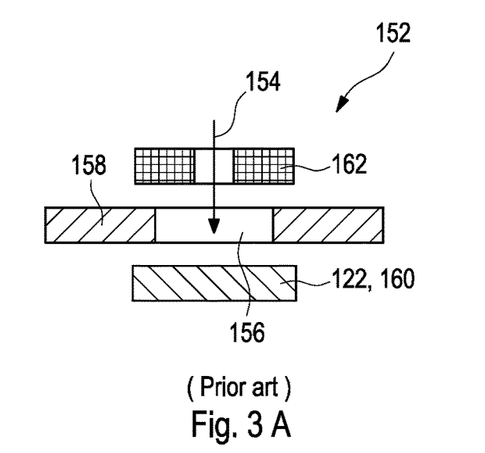
FIGS. 3A-3D schematically demonstrate a particular advantage of the electrochemical sensor according to this disclosure compared to an electrochemical sensor according to the state of the art.

Further, FIG. 3 schematically demonstrates the advantage of the electrochemical sensor 110 with regard to facilitating the positioning of the plurality of the enzyme fields 140 on the substrate 114 compared to a prior art electrochemical sensor 152 as manufactured according to the state of the art.

For depositing 154 an enzyme paste very accurately into openings 156 comprised by an electrically insulating layer 158 in order to thoroughly cover an electrically conducting surface 160 of the working electrode 122 by screen printing, a silkscreen 162 is used for manufacturing the electrochemical sensor 152 according to the state of the art as shown in FIG. 3A. However, this method is applicable only as long as the electrically insulating layer 158 is very well positioned with respect to the electrically conducting surface 160 of the working electrode 122 and silkscreen 162. As can be seen in FIG. 3B, a lateral shift 164 of the electrically insulating layer 158 may result in a positioning which does not allow manufacturing the working electrode 122 as required.

In contrast, as illustrated in FIGS. 3C and 3D, a lateral shift 164 of the electrically insulating layer 158 may still allow manufacturing the working electrode 122 in the design as proposed herein for the electrochemical sensor 110 since overprinting of the enzyme paste replaces imprinting of the enzyme paste into the openings 156 as known from the state of the art. By providing the at least one conductive trace 132 in the previous openings 156 of the electrically insulating layer 158, depositing 154 the enzyme paste very accurately on top of the at least one conductive trace 132 becomes rather easy, in particular, when the at least one conductive trace 132 is, additionally, provided in the form of the grid 150.

While exemplary embodiments have been disclosed hereinabove, the present invention is not limited to the disclosed embodiments. Instead, this application is intended to cover any variations, uses, or adaptations of this disclosure using its general principles. Further, this application is intended to cover such departures from the present disclosure as come within known or customary practice in the art to which this invention pertains and which fall within the limits of the appended claims.

LIST OF REFERENCE NUMBERS 110 electrochemical sensor
111 sensor system
112 front side
114 substrate
116 proximal region
118 distal region
120 contact elements
121 measurement device
122 working electrode
124 counter electrode
126 reference electrode
128 backside
130 lead wire
132 conductive trace
134 layer of a non-corrosive bonding agent
136 first partition
138 second partition
140 enzyme field
142 gap
144 first profile
146 second profile
148 solder resist
150 grid
152 prior art electrochemical sensor
154 depositing
156 opening
158 insulating layer
160 conducting surface
162 silkscreen
164 lateral shift

What is claimed is:

1. An electrochemical sensor for detecting an analyte in a sample of a body fluid, comprising:
   a substrate having proximal and distal regions, the proximal region having at least one contact element configured to communicate with a measurement device;
   a working electrode located in the distal region and having a conductive trace;
   a counter electrode; and
   a plurality of enzyme fields, each enzyme field comprising an enzyme configured for providing a reaction with the analyte, wherein the enzyme fields are spaced apart and each enzyme field is partially located on the conductive trace, further wherein at least one of the enzyme fields extends outside one or both edges of the trace, wherein the substrate further comprises a front side and a back side, wherein the working electrode is located on the front side of the substrate and the counter electrode is located on one of the front side or the back side of the substrate.

2. The electrochemical sensor according to claim 1, wherein the working electrode comprises a multiplicity of conductive traces that form a grid.

3. The electrochemical sensor according to claim 1, wherein the conductive trace comprises a non-corrosive, electrically conducting material.

4. The electrochemical sensor according to claim 3, wherein the non-corrosive, electrically conducting material includes gold.

5. The electrochemical sensor according to claim 1, wherein the conductive trace is located on a layer comprising a non-corrosive bonding agent which is located on the substrate.

6. The electrochemical sensor according to claim 5, wherein the non-corrosive bonding agent is selected from at least one of titanium or palladium.

7. The electrochemical sensor according to claim 1, wherein the conductive trace comprises a first partition located in the distal region and a second partition located in the proximal region, wherein at least the first partition of the conductive trace is devoid of copper.

8. The electrochemical sensor according to claim 7, wherein the second partition of the conductive trace comprises copper as one of the electrically conducting material or the bonding agent for a further electrically conducting material.

9. The electrochemical sensor according to claim 1, wherein the substrate is partially covered by a solder resist, wherein the solder resist at least partially covers the proximal region of the substrate.

10. The electrochemical sensor according to claim 9, wherein the distal region of the substrate is devoid of the solder resist.

11. The electrochemical sensor according to claim 1, wherein the substrate is a flexible substrate comprising a bendable electrically insulating material.

12. The electrochemical sensor according to claim 1, wherein the bendable electrically insulating material comprises at least one of polyimide (PI), polyethylene terephthalate (PET), polyethylene naphthalate (PEN), polypropylene (PP), polyamide (PA), flexible glass, or silicon.

13. The electrochemical sensor according to claim 1, wherein the substrate further comprises a front side and a back side, wherein the working electrode is located on the front side of the substrate and the counter electrode is located on one of the front side or the back side of the substrate.

14. The electrochemical sensor according to claim 1, further comprising a reference electrode located in the proximal region of the substrate.

15. The electrochemical sensor according to claim 1, wherein each of the enzyme fields comprises glucose oxidase and/or glucose dehydrogenase as the enzyme, manganese dioxide as a catalyst, carbon particles, and a polymer binder.

16. The electrochemical sensor according to claim 1, wherein at least one of the enzyme fields does not cover the entire width of the trace.

17. A sensor system for electrochemically detecting an analyte in a sample of a body fluid, the sensor system comprising:
   an electrochemical sensor according to claim 1;
   a measurement device;
   at least one contact element configured for providing interoperation between the electrochemical sensor and the measurement device, wherein the measurement device is, in interoperation with the electrochemical sensor, configured for performing at least one electrical measurement, and wherein the measurement device is further configured for determining an analyte value in the sample of the body fluid by evaluating the electrical measurement.

18. An electrochemical sensor for detecting an analyte in a sample of a body fluid, comprising:
   a substrate having proximal and distal regions, the proximal region having at least one contact element configured to communicate with a measurement device;
   a working electrode located in the distal region and having a conductive trace;
   a counter electrode; and
   a plurality of enzyme fields, each enzyme field comprising an enzyme configured for providing a reaction with the analyte, wherein the enzyme fields are spaced apart and each enzyme field is partially located on the conductive trace, wherein at least one of the enzyme fields extends outside one or both edges of the trace, and wherein at least one of the enzyme fields does not cover the entire width of the trace.

19. A method for manufacturing an electrochemical sensor, the method comprising:
   a) providing a substrate having proximal and distal regions;
   b) providing contact elements in the proximal region, the contact elements configured to communicate with a measurement device;
   c) placing a conductive trace in the distal region;
   d) generating at least one working electrode by placing a plurality of enzyme fields on the conductive trace, wherein each enzyme field comprises at least one enzyme configured for providing a reaction with an analyte, further wherein at least one of the enzyme fields extends outside one or both edges of the trace;
   e) placing at least one counter electrode on the substrate; and
   f) providing respective electrical connections from each of the conductive traces and the counter electrode to the contact elements, wherein at least one of the enzyme fields is deposited such that it does not cover the entire width of the trace.

20. A method for manufacturing an electrochemical sensor, the method comprising:
   a) providing a substrate having proximal and distal regions;
   b) providing contact elements in the proximal region, the contact elements configured to communicate with a measurement device;
   c) placing a conductive trace in the distal region;
   d) generating at least one working electrode by placing a plurality of enzyme fields on the conductive trace, wherein each enzyme field comprises at least one enzyme configured for providing a reaction with an analyte, further wherein at least one of the enzyme fields extends outside one or both edges of the trace;
   e) placing at least one counter electrode on the substrate;
   f) providing respective electrical connections from each of the conductive traces and the counter electrode to the contact elements; and
   g) providing an insulating layer that overlays the conductive trace and providing openings in the insulating layer, wherein step d) comprises overprinting an enzyme paste onto the insulating layer around the openings to thereby form the enzyme fields, whereby manufacturing tolerances can be reduced.

* * * * *